(12) United States Patent
Namba (10) Patent No.: US 8,541,179 B2
(45) Date of Patent: Sep. 24, 2013

(54) IMMUNODETECTION ASSAY FOR MYCOBACTERIUM TUBERCULOSIS COMPLEX

(75) Inventor: Yasuharu Namba, Numazu (JP)

(73) Assignee: BL Co., Ltd., Shizuoka (JP)

( * ) Notice: Subject to any disclaimer, the term of this patent is extended or adjusted under 35 U.S.C. 154(b) by 378 days.

(21) Appl. No.: 12/810,217

(22) PCT Filed: Dec. 19, 2008

(86) PCT No.: PCT/JP2008/073200
§ 371 (c)(1),
(2), (4) Date: Jun. 23, 2010

(87) PCT Pub. No.: WO2009/084481
PCT Pub. Date: Jul. 9, 2009

(65) Prior Publication Data
US 2010/0285506 A1   Nov. 11, 2010

(30) Foreign Application Priority Data
Dec. 28, 2007   (JP) .................. 2007-339376

(51) Int. Cl.
G01N 33/53   (2006.01)
A61K 39/40   (2006.01)
A61K 39/04   (2006.01)

(52) U.S. Cl.
USPC ... 435/7.1; 424/130.1; 424/139.1; 424/141.1; 424/150.1; 424/184.1; 424/185.1; 424/234.1; 424/248.1; 435/7.2

(58) Field of Classification Search
USPC .......... 424/130.1, 139.1, 141.1, 150.1, 184.1, 424/185.1, 234.1, 248.1; 435/7.2, 7.1
See application file for complete search history.

(56) References Cited

U.S. PATENT DOCUMENTS

| | | | |
|---|---|---|---|
| 6,458,366 | B1 | 10/2002 | Reed et al. |
| 6,949,246 | B2 | 9/2005 | Reed et al. |
| 7,122,196 | B2 | 10/2006 | Reed et al. |
| 7,906,277 | B2 | 3/2011 | Reed et al. |
| 2003/0135026 | A1 | 7/2003 | Reed et al. |
| 2005/0181419 | A1 | 8/2005 | Reed et al. |
| 2007/0141087 | A1 | 6/2007 | Reed et al. |

FOREIGN PATENT DOCUMENTS

| | | |
|---|---|---|
| CN | 101294964 A | 10/2008 |
| JP | H01-247094 A | 10/1989 |
| JP | 07-110332 A | 4/1995 |
| JP | H11-108931 A | 4/1999 |
| JP | 2007-316068 A | 12/2007 |

OTHER PUBLICATIONS

International Preliminary Report on Patentability dated Aug. 10, 2010 for application PCT/JP2008/073200.
International Search Report issued on Jan. 20, 2009 in International Application No. PCT/JP2008/073200.
Abe et al., Simple and rapid identification of *Mycobacterium tuberulosis* complex by immunochromatographic assay using anti-MPB64 monoclonal antibodies, Journal of Clinical Microbiology, Nov. 1999, pp. 3693-3697.
M. Hasegawa et al., "Evaluation of Rapid Identification Method for *Mycobacterium tuberculosis* Complex using the Immunochromatographic Slide Test Kit", Kansenshogaku Zasshi, Feb. 2003, 77(2), pp. 110-115.
D. Hillemann et al., "Application of the Capilia TB assay for culture confirmation of *Mycobacterium tuberculosis* complex isolates", International Journal of Tuberculosis and Lung Disease, vol. 9(12), 2005 The Union, pp. 1409-1411.
N. Hasegawa et al., "New Simple and Rapid Test for Culture Confirmation of *Mycobacterium tuberculosis* Complex: a Multicenter Study", Journal of Clinical Microbiology, Mar. 2002, pp. 908-912.
Shulman, Nature, vol. 276, pp. 269-270 (Nov. 16, 1978).
Supplementary European Search Report dated Jun. 5, 2012, issued against EP Application No. 08866382.8.
Jann-Yuan Wang et al., :Performance assesment of Capilia TB assay and the BD ProbeTec ET system for rapid culture confirmation of *Mycobacterium tuberculosis*, Diagnosis Microbiology and Infectious Disease, vol. 59, (2007), pp. 395-399.
Second Office Action dated Dec. 27, 2012, issued by The State Intellectual Property Office of P.R. China against CN Patent Application No. 200880125685.5.

*Primary Examiner* — Rodney P. Swartz
(74) *Attorney, Agent, or Firm* — Fitch, Even, Tabin & Flannery, LLP (57) ABSTRACT

The present invention provides a method for specifically detecting a *Mycobacterium tuberculosis* complex-specific secretory protein MPT64 antigen in a biological sample, whereby diagnosis of infection with *Mycobacterium tuberculosis* is carried out rapidly and safely with higher accuracy than before. An antibody that recognizes an epitope for MPB64 located in any one of amino acid sequences of SEQ ID NOS: 2 to 4, particularly a monoclonal antibody was obtained. Thus, an immunoassay using the antibody, particularly a sandwich immunoassay using first and second antibodies to MPB64, particularly an immunochromatographic assay and an immunochromatographic test strip are provided. A biological sample can be rapidly subjected to the immunoassay without culturing or after culturing for a time before *Mycobacterium tuberculosis* complex bacteria in the sample substantially start to grow. The biological sample may be pretreated by treatment for inactivation of *Mycobacterium tuberculosis*, or treatment by dispersion or solubilization.

37 Claims, 1 Drawing Sheet

IMMUNODETECTION ASSAY FOR *MYCOBACTERIUM TUBERCULOSIS* COMPLEX

CROSS-REFERENCE TO RELATED APPLICATIONS

This application is a National Phase Entry of International Application No. PCT/JP2008/073200, filed Dec. 19, 2008, which claims foreign priority to Japanese Patent Application No. 2007-339376, filed Dec. 28, 2007. The complete disclosures of the referenced applications, including sequence listings, are incorporated herein by reference.

TECHNICAL FIELD

The present invention relates to an immunodetection assay using an antibody to a *Mycobacterium tuberculosis* complex-specific secretory protein MPB64, and more specifically relates to a sandwich immunoassay, and particularly an immunochromatographic assay and an immunochromatographic test strip. The present invention relates to a detection method useful for rapid, safe and highly accurate diagnosis of infection with *Mycobacterium tuberculosis* complex by detecting *Mycobacterium tuberculosis* complex specifically with high sensitivity.

BACKGROUND ART

MPB64 is a Mycobacterial protein which is produced by *Mycobacterium bovis* BCG and secreted outside of bacteria cells. Also, MPT64 is known as one of the Mycobacterial proteins that are specifically produced by *Mycobacterium tuberculosis* and secreted outside of bacteria cells. It is known that MPT64 is the same substance as MPB64. This means that an antibody to MPB64 is also an antibody to MPT64.

Therefore, infection with *Mycobacterium tuberculosis* complex can be diagnosed by culturing pathogenically harmless *Mycobacterium bovis* BCG, extracting and purifying MPB64 produced in the culture, obtaining an anti-MPB64 antibody using the MPB64 as an antigen, and detecting MPT64 in a sample by antigen-antibody reaction (immune reaction) using this antibody.

A method for detecting *Mycobacterium tuberculosis* by immunological method using an antibody to MPB64 (hereinafter, abbreviated as "anti-MPB64 antibody") is already known (refer to Patent Document 1). In addition, an assay utilizing immunochromatography is also already known as the immunological method (refer to Patent Document 2).

However, these known methods require *Mycobacterium tuberculosis* complex in a sample to grow by culturing to secrete MPT64 before it is subjected to immunoassay, and the culturing takes about a week.

In addition, even though the conventional immunochromatographic methods have no reactivity with most of non-tuberculous *Mycobacteria* (NTB) but have a very strong reactivity with *Mycobacterium tuberculosis* complex, it has been reported that they still show cross reactivity with two strains of non-tuberculous *Mycobacteria*, i.e., *Mycobacterium marinum* and *Mycobacterium flavescens* (Non-Patent Document 1).

Patent Document 1: Japanese Patent Laid-open No. H07-110332
Patent Document 2: Japanese Patent Laid-open No. H11-108931
Non-Patent Document 1: ABE C. et al., "Simple and Rapid Identification of the *Mycobacterium tuberculosis* Complex by Immunochromatographic Assay Using Anti-MPB64 Monoclonal Antibodies", Journal of Clinical Microbiology, November 1999, p. 3693-3697

DISCLOSURE OF THE INVENTION

Problems to be Solved by the Invention

The object of the present invention is to specifically detect MPT64 antigen in a biological sample, so that diagnosis of infection with *Mycobacterium tuberculosis* complex can be carried out with higher accuracy than before.

In addition, another object of the present invention is to detect MPT64 antigen in a biological sample with high sensitivity, so that the biological sample can be subjected to an immunoassay as it is without culturing or after culturing for a time before *Mycobacterium tuberculosis* complex bacteria in the sample substantially start to grow, and diagnosis of infection with *Mycobacterium tuberculosis* complex can be carried out more rapidly and safely than before.

Means for Solving the Problem

The present inventor has succeeded in obtaining an antibody to a specific epitope of MPB64 by immunizing mice with MPB64 as an immunogen, and has found that *Mycobacterium tuberculosis* complex can be detected more specifically with higher sensitivity than before by using the aforementioned antibody in an immunoassay, particularly in a sandwich immunoassay, and specifically in an immunochromatographic assay. Thus, the present invention has been completed.

That is, according to one aspect of the present invention, there is provided a method for detecting *Mycobacterium tuberculosis* complex, which comprises an immunoassay using an antibody to a *Mycobacterium tuberculosis* complex-specific secretory protein MPB64, in which said antibody comprises an antibody to an epitope for MPB64 located in any one of amino acid sequences of SEQ ID NOS: 2 to 4.

The immunoassay used in this detecting method is not particularly limited, but a sandwich immunoassay, particularly, an ELISA (Enzyme-linked immunosorbent assay) method, an immunochromatographic assay, and the like are preferable.

Therefore, according to another aspect of the invention, there is provided a method for detecting *Mycobacterium tuberculosis* complex, which comprises a sandwich immunoassay using first and second antibodies to a *Mycobacterium tuberculosis* complex-specific secretory protein MPB64, in which at least one of the first antibody and second antibodies comprises an antibody to an epitope for MPB64 located in any one of amino acid sequences of SEQ ID NOS: 2 to 4.

In addition, according to a preferable embodiment of the present invention, there is provided an immunochromatographic assay for detecting *Mycobacterium tuberculosis* complex, which comprises:

providing a membrane carrier having a capturing zone which is formed in a predetermined position thereof by immobilizing a first antibody to a *Mycobacterium tuberculosis* complex-specific secretory protein MPB64; and chromatographically developing a mixed solution containing a second antibody to the MPB64 and a predetermined amount of a test sample in the membrane carrier toward the capturing zone, whereby a complex of an antigen contained in the test sample and the second antibody is captured in the capturing zone, and wherein at least one of the first and second antibodies comprises an antibody to an epitope for MPB64 located in any one of amino acid sequences of SEQ ID NOS: 2-4.

Further, according to a preferable embodiment of the present invention, there is provided an immunochromatographic test strip for detecting Mycobacterium tuberculosis complex, which at least comprises first and second antibodies to a Mycobacterium tuberculosis complex-specific secretory protein MPB64, and a membrane carrier, wherein the first antibody is previously immobilized in a predetermined position of the membrane carrier so as to form a capturing zone, and the second antibody is labeled with a suitable labeling agent and is prepared at a position remote from the capturing zone for being chromatographically developed in the membrane carrier, wherein at least one of the first and second antibodies comprises an antibody to an epitope for MPB64 located in any one of amino acid sequences of SEQ ID NOS: 2 to 4.

The antibody to MPB64 which is indispensably used in the present invention is an antibody to an epitope for MPB64 which is located in any one of amino acid sequences of SEQ ID NOS: 2-4, and may be a polyclonal antibody or a monoclonal antibody, and is preferably a monoclonal antibody from the viewpoint of reaction specificity. Meanwhile, the amino acid sequences of SEQ ID NOS: 2-4 constitute parts of the whole amino acid sequence of MPB64 shown in SEQ ID NO: 1, and are regions containing epitopes of MPB64.

In case of a sandwich immunoassay such as an immunochromatographic assay, the respective first and second antibodies used therein may be polyclonal or monoclonal, and it is generally preferable that at least one of the two antibodies is monoclonal, and particularly preferable that both of the two antibodies are monoclonal, from the viewpoint of reaction specificity. Also, since MPB64 is a monomeric protein, it is preferable that the first and second antibodies are antibodies to different epitopes of MPB64.

The antibody used in the present invention is an antibody to an epitope which is located in any one of amino acid sequences of SEQ ID NOS: 2-4 contained in the whole amino acid sequence of MPB64 shown in SEQ ID NO: 1, and therefore, specifically reacts with MPB64 or MPT64. Also, these antibodies of the present invention do not react with non-tuberculous Mycobacterium (NTB), and further do not react with Mycobacterium marinum and Mycobacterium flavascens, and thus are excellent in specificity. The amino acid sequences of SEQ ID NOS: 2-4 are regions containing epitopes of MPB64. In other words, the antibody used in the present invention may be an antibody which undergoes antigen-antibody reaction with a fragment of MPB64 having 12-15 amino acid residues that encompass one of amino acid sequences of SEQ ID NOS: 2-4.

Thus, according to another aspect of the present invention, there is provided a monoclonal antibody which recognizes an epitope of MPB64 which is located in any one of amino acid sequences of SEQ ID NOS: 2-4.

Effect of the Invention

According to the present invention, an antibody to an epitope which is located in any one of amino acid sequences of SEQ ID NOS: 2-4 contained in the whole amino acid sequence of MPB64 shown in SEQ ID NO: 1 is used in a detection method with an immunoassay, and thus diagnosis of infection with Mycobacterium tuberculosis complex can be carried out with higher accuracy than before, and also a biological sample can be subjected to the immunoassay as it is without culturing or after culturing for a time before Mycobacterium tuberculosis complex bacteria in the sample substantially start to grow, so that the diagnosis of infection with Mycobacterium tuberculosis complex can be carried out more rapidly and safely than before.

In addition, according to the immunochromatographic assay and immunochromatographic test strip of the present invention, diagnosis of infection with Mycobacterium tuberculosis complex can be carried out rapidly and safely with higher accuracy than before without need of special devices and skilled techniques, and risk of secondary infection is reduced.

BEST MODE FOR CARRYING OUT THE INVENTION

In the present invention, production of an antibody and each step of the detection method and assay using the antibody are respectively conducted in accordance with known immunological techniques.

In the present invention, a polyclonal antibody can be obtained, for example, by cloning a DNA fragment corresponding to an amino acid sequence of SEQ ID NOS: 2-4 from a DNA sequence encoding the amino acid sequence shown in SEQ ID NO: 1, allowing the cloned gene to express in a host such as Escherichia coli in a genetic engineering manner, extracting and purifying the expressed protein, and immunizing an animal with the purified protein being used as an antigen according to an ordinary method, and then obtaining the polyclonal antibody from the antiserum of the immunized animal.

In the present invention, a monoclonal antibody can be obtained, for example, by immunizing an animal such as a mouse with the above purified protein being used as an antigen, fusing the splenic cells of the immunized animal with myeloma cells for cell fusion, selecting the thus fused cells in a HAT-containing medium and allowing them to grow, and then selecting the grown strains using the above purified protein by an enzyme-labeled immunoassay or the like.

Alternatively, the monoclonal antibody can be obtained, for example, by immunizing an animal such as a mouse with MPB64 which is purified from culture supernatant of Mycobacterium bovis BCG being used as an antigen, fusing the splenic cells of the immunized animal with myeloma cells for cell fusion, selecting the thus fused cells in a HAT-containing medium and allowing them to grow, and then selecting a strain reactive with a polypeptide of SEQ ID NOS: 2-4 from the grown strains.

An immunochromatographic assay of the present invention for detecting existence of Mycobacterium tuberculosis complex in a test sample can be practiced easily in accordance with a structure of a known immunochromatographic test strip.

Generally, such an immunochromatographic test strip is constituted by at least a first antibody which is capable of undergoing antibody-antigen reaction at a first antigenic determinant of an antigen, a second antibody which is labeled and capable of undergoing antibody-antigen reaction at a second antigenic determinant of the antigen, and a membrane carrier, wherein the first antibody is previously immobilized in a predetermined position of the membrane carrier so as to form a capturing zone, and the second antibody is prepared at a position remote from the capturing zone for being chromatographically developed in the membrane carrier. Each of the aforementioned first and second antibodies may be either polyclonal antibody or monoclonal antibody, but it is preferable that at least one of them is monoclonal antibody. Since MPB64 is a monomeric protein, the first and second antibodies are used in a combination of "hetero", that is, the first and second antibodies which recognize the respective antigenic determinants different in both position and structure on an antigen are used in combination. For example, when a monoclonal antibody to an epitope for MPB64 which is located in the amino acid sequence of SEQ ID NO: 2 is used as the first antibody, a monoclonal antibody to an epitope for MPB64 which is located in the amino acid sequence of SEQ ID NO: 3 or 4 is used as the second antibody.

Figure 1:
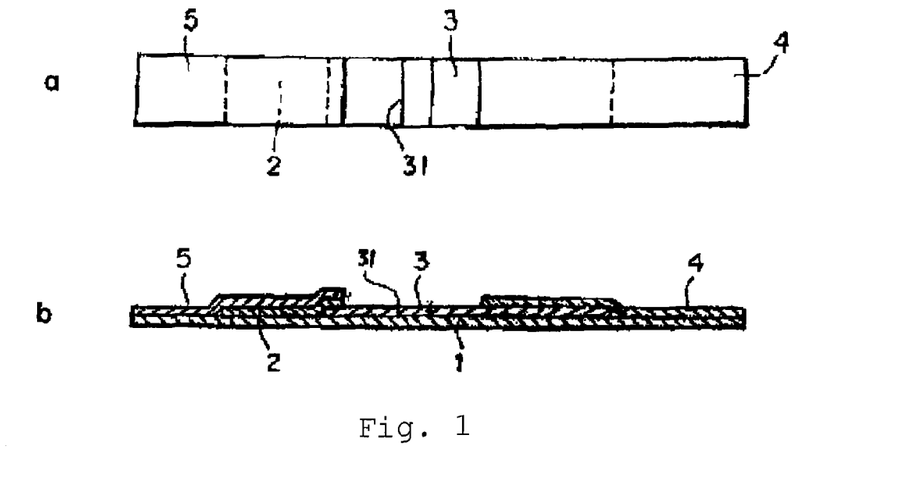

As a specific example of an immunochromatographic test strip, mention may be made of, for example, a test strip as shown in FIG. 1. In FIG. 1, the numeral 1 indicates an adhesive sheet, 2 indicates an impregnated member, 3 indicates a membrane carrier, 31 indicates a capturing zone, 4 indicates an adsorbing member, and 5 indicates a sample-receiving member.

In the example shown in the figure, the membrane carrier 3 consists of an elongated strip-shaped nitrocellulose membrane filter having a width of 5 mm and a length of 36 mm.

The membrane carrier 3 has a first antibody which is immobilized at a position of 7.5 mm from the end on the starting side of chromatographic development, so as to form a capturing zone 31 of an analyte.

In the example shown in the figure, a nitrocellulose membrane filter is used as the membrane carrier 3. However, any type of membrane carrier can be used herein, as long as it is able to chromatographically develop an analyte contained in a test sample and immobilize an antibody that forms the capturing zone 31. Thus, other types of cellulose membranes, nylon membranes, glass fiber membranes, or the like can also be used.

The impregnated member 2 comprises a member in which a second antibody capable of undergoing antibody-antigen reaction with the antigen at a second antigenic determinant positioned at a site different from the first antigenic determinant to which the first antibody is attached is arranged by means of impregnation or the like. The second antibody is previously labeled with a suitable labeling agent.

In the example as shown in the figure, a strip-shaped glass fiber nonwoven fabric having a size of 5 mm×15 mm is used as the impregnated member 2. However, the impregnated member 2 is not limited thereto, but includes, for example, cellulose fabrics (a filter, a nitrocellulose membrane, etc.), porous plastic fabrics such as of polyethylene and polypropylene, and others.

As a labeling agent that labels the second antibody, any substance can be used, as long as it is usable herein. Examples of such a labeling agent include a color labeling agent, and an enzyme labeling agent, and a radiation labeling agent.

Of these, a color labeling agent is preferably used because observation of a color change in the capturing zone 31 with naked eyes enables rapid and simple determination. Also, from the viewpoint of improvement in sensitivity, it is preferable that an observation of the capturing zone 31 can be conducted using a fluorescent immunochromatographic reader with a fluorescent labeling agent.

Examples of such a color labeling agent include metallic colloidal particles such as gold colloidal particles, platinum colloidal particles and platinum-gold complex colloidal particles, synthetic latex particles such as polystyrene latex colored with a red or blue pigment, and latex particles such as natural rubber latex. Of these, metallic colloidal particles such as a gold colloidal particle are particularly preferable.

Examples of a fluorescent labeling agent include direct labeling agents such as FITC and rhodamine as well as a fluorescent latex particle containing a fluorescent compound and a compound such as a quantum dot. Of these, a fluorescent latex particle containing a fluorescent compound is preferable. Also, excitation wavelength and fluorescence wavelength of the fluorescent compound are not particularly limited, but a fluorescent compound large in the so-called Stokes shift in which excitation wavelength is far from measured wavelength is preferably used from the viewpoint of setting of the measurement device.

The impregnated member 2 can be produced by absorbing a suspension of a labeled second antibody into a member such as the aforementioned glass fiber nonwoven fabric, and then drying it.

As shown in FIG. 1, the immunochromatographic test strip of the present invention can be produced as follows. The membrane carrier 3 is affixed to the middle of the adhesive sheet 1. On the end on the starting side of chromatographic development (that is, the left side in FIG. 1 which is hereinafter referred to as an "upstream side" whilst the opposite side, that is, the right side in FIG. 1 is hereinafter referred to as a "downstream side") of the membrane carrier 3, the downstream side end of the impregnated member 2 is laid so as to communicate them. The upstream side zone of the impregnated member 2 is affixed to the adhesive sheet 1.

Moreover, if necessary, the downstream side zone of a sample-receiving member 5 may be placed on the upper face of the impregnated member 2 whilst the upstream side zone of the sample-receiving member 5 may also be affixed to the adhesive sheet 1. Furthermore, the upstream side zone of an absorbing member 4 may be placed on the upper face of the downstream side zone of the membrane carrier 3 whilst the downstream side zone of the absorbing member 4 may be affixed to the adhesive sheet 1.

As the sample-receiving member 5, may be used, for example, a sheet or film of a porous synthetic resin such as porous polyethylene and porous polypropylene, or cellulose paper or a woven or nonwoven fabric such as a filter and a cotton fabric.

The absorbing member 4 may be made of any material as long as it is able to quickly absorb and retain a liquid. Examples of such a material include cotton fabrics, filter paper, and porous plastic nonwoven fabrics made from polyethylene, polypropylene, etc. In particular, filter paper is optimal.

Further, in case of commercially available products, the immunochromatographic test strip as shown in FIG. 1 is supplied such that the test strip is housed in a suitable plastic casing having a test sample-injecting zone and a determining zone opened above the sample-receiving member 5 and the capturing zone 31, respectively.

Thus, a test sample containing a biological sample or the like is, if required, mixed with a suitable developing solvent so as to obtain a mixed solution that can be developed chromatographically. Thereafter, the mixed solution is injected into the sample-receiving member 5 of the immunochromatographic test strip as shown in FIG. 1, so that it passes through the sample-receiving member 5 and is mixed with a labeled second antibody at the impregnated member 2.

In this instance, if an analyte exists in the aforementioned mixed solution, a complex of an analyte and the second antibody is formed as a result of antigen-antibody reaction.

This complex is developed chromatographically in the membrane carrier 3, and then reaches the capturing zone 31. Thus, the complex is captured by the first antibody immobilized therein as a result of antigen-antibody reaction.

In this instance, if a color labeling agent such as gold colloidal particles is used as a labeling agent, the analyte can be immediately determined qualitatively or quantitatively based on coloring caused by accumulation of the color labeling agent at the capturing zone 31. When a fluorescent labeling agent is used as a labeling agent, the amount of fluorescence of the fluorescent agent accumulated in the capturing zone 31 is read by a measuring device, so that it can be measured quantitatively.

Meanwhile, in the present invention, the second antibody may be prepared for being chromatographically developed in the membrane carrier by storing the second antibody or the impregnated member containing the second antibody in a suitable container so as to be injected to the membrane carrier after mixing the test sample and the second antibody in the container instead of arranging the second antibody or the impregnated member on a membrane carrier.

The biological sample used for preparing the test sample is not particularly limited, but includes, for example, a body fluid collected from a living body such as sputum, pleural effusion, bronchial secretory, gastric juices, blood, spinal fluid, urine and feces, and preferably used is sputum. Also, bronchial washings collected when a test of respiratory organs was conducted and tissue pieces collected from a bronchi or lung can be used as a biological sample. Further, a culture and bacteria obtained by culturing the biological sample collected above with a solid culture medium or a liquid culture medium can be applied. Moreover, a culture in which a biological sample is cultured for a time before *Mycobacterium tuberculosis* complex bacteria substantially starts to grow can be applied, and in this case, a little amount of a liquid culture medium is preferably used as a culture medium. The biological sample may be used as it is as a test sample, but may be diluted with a suitable diluent such as a developing solvent to obtain a test sample.

The culture of a biological sample can be conducted in accordance with an ordinary method in case of both liquid culture and solid culture, and the a liquid culture is preferable since the culture (that is a culture solution) can be applied to immunoassays such as an immunochromatographic assay.

The liquid culture medium used for liquid culture is not particularly limited as long as it can culture the above biological sample, and for example, a culture medium described in Guideline for *Mycobacterium* Examination can be used. Concrete examples include Middlebrook 7H9 broth, Dubos liquid medium (a product of Becton, Dickinson and Company), MGIT (a product of Becton, Dickinson and Company) and BactAlert (a product of bioMérieux).

The solid culture medium used for solid culture is not particularly limited as long as it can culture the above biological sample, and for example, a culture medium described in Guideline for *Mycobacterium* Examination can be used. Concrete examples include Ogawa medium and Kudo PD slant medium in test tube (a product of Kyowa Pharmaceutical CO., Ltd.). A culture resulting from solid culture can be used for the immunological assay by diluting with a diluent such as a physiological saline solution and phosphate buffer.

Incubation temperature is preferably around 37° C. for both liquid culture and solid culture. Incubation time may be a time sufficient for secreting a detectable amount of a *Mycobacterium tuberculosis* specific secretory protein which is used as a *Mycobacterium tuberculosis* marker, and usually 2-10 days and preferably 2-7 days.

The liquid culture can be conducted, for example, by placing 100 µl to 5 ml of a liquid culture medium in a 1 ml to 10 ml culture vessel, and aerobically shaking it for the above incubation time period.

In addition, the biological sample and the culture may be subjected to a pretreatment with a suitable method before subjected to the test, in order to suppress denaturation of the *Mycobacterium tuberculosis* complex-specific secretory protein and place it in a condition suitable for immunoassay. The pretreatment include, for example, inactivation treatment or dispersion or solubilization treatment of the *Mycobacterium tuberculosis* complex.

The inactivation treatment of the *Mycobacterium tuberculosis* complex includes, for example, a heat treatment and a filtration treatment, and preferably a heat treatment. Heating temperature is not particularly limited, but usually 50° C.-140° C. and preferably 100° C. Also, heating time is not particularly limited, but usually 1-60 minutes and preferably 15-30 minutes. The heat treatment can be conducted by subjecting the whole vessel containing a biological sample to autoclave treatment. The inactivation treatment of the *Mycobacterium tuberculosis* makes it possible to conduct the examination without use of a safety cabinet.

The solubilization treatment is conducted mainly for the purpose of lowering the viscosity of a biological sample such as sputum, and for example, is conducted by adding, to the biological sample, a reagent capable of solubilizing a constituent of the biological sample. Such a reagent includes, for example, an alkali substance, a reducing substance, a protease and a surface active agent and preferably an alkali substance, a reducing substance and a protease.

The alkali substance includes sodium hydroxide, and a concentration thereof is not particularly limited, but in view of denaturation of the *Mycobacterium tuberculosis*-specific secretory protein, it is preferably used in a concentration of 0.5 N to 2 N.

The reducing substance includes, for example, N-acetyl-L-cysteine (NALC) and dithiothreitol, and a concentration thereof is not particularly limited, but it is preferably used in 0.05% to 1%. Also, it is more effective to use the alkali substance and the reducing substance in combination.

The protease includes, for example, a semi-alkali protease (product name: SPUTAZYME manufactured by KYOKUTO PHARMACEUTICAL INDUSTRIAL CO., LTD.).

The dispersion treatment includes known physical treatment methods, for example, stirring operation using a vortex mixer or the like, preferably stirring using a vortex mixer or the like with addition of glass beads to the biological sample.

The dispersion treatment and the solubilization treatment can be conducted alone or in combination.

When whole blood is used as a test sample, it is preferred that a hematocyte-capturing membrane member is disposed in the aforementioned sample-receiving member if a color labeling agent such as gold colloidal particles is particularly used as a labeling agent for a labeled antibody. Such a hematocyte-capturing membrane member is preferably laminated between the aforementioned impregnated member and the aforementioned sample-receiving member. This inhibits development of erythrocytes in the membrane carrier and thus facilitates the confirmation of accumulation of color labeling agents in the capturing zone of the membrane carrier. As such a hematocyte-capturing membrane member, a carboxymethyl cellulose membrane is used. Specifically, an ion exchange filter CM (trade name) available from Advantec Toyo K.K., an ion exchange cellulose paper available from Whatman Japan K.K., etc can be used.

EXAMPLE

The present invention will be more specifically described in the following examples. However, these examples are not intended to limit the scope of the present invention.

Example 1

Production of Anti-MPB64 Monoclonal Antibody

MPB64 was purified from a culture supernatant which was obtained by culturing the *Mycobacterium bovis* BCG Tokyo strain in Middlebrook 7H11 broth. Monoclonal antibodies to the protein were produced using the resulting MPB64 as an antigen. Such monoclonal antibodies were produced according to an ordinary method.

That is, 100 μg of the purified MPB64 was mixed with the same amount of Adjuvant Complete Freund (Difco). Thereafter, a mouse (BALB/c, 5-week-old, Japan SLC, Inc.) was immunized with the mixture 3 times, and splenic cells thereof were then used for cell fusion. For such cell fusion, Sp2/0-Ag14 cells (Shulman et al., Nature, 276:269-279 (1978)) that were mouse myeloma cells were used.

The resulting fused cells were grown after selected in a HAT-containing medium, and finally 3 clones of monoclonal antibody-producing cells reactive with MPB64 were obtained from the grown fused cells. Hereinafter, the antibodies yielded by the respective clones are referred to as monoclonal antibodies TB001, TB002 and TB003.

Example 2

Epitope Analysis of Anti-MPB64 Antibody

Total 73 polypeptides were produced by SPOT peptide synthesis, which were each composed of a unit of 12 amino acids with a frame shift of 3 amino acids from the N-terminal of the amino acid sequence of MPB64 of SEQ ID NO: 1 derived from *Mycobacterium tuberculosis* H37RV strain. Meanwhile, each amino acid sequence was selected such that a proline was not selected as the starting amino acid due to the peptide synthesis by SPOT. Then, a SPOT sheet (manufactured by JST and Sigma Aldrich) in which the above 73 polypeptides were immobilized onto a cellulose membrane was produced. The SPOT sheet was incubated on the shaking table for 2 hours, and then for an hour with a blocking buffer (50 mM Tris HCl, 140 mM NaCl, 5 mM NaEDTA, 0.05% NP40 (Fluka), 0.25% gelatin (Sigma), 1% bovine serum albumin (Sigma), pH 7.4) containing 2 μg/ml of the monoclonal antibodies which were produced in Example 1, to incubate and react. After the reaction was completed, the SPOT sheet was washed with PBS (10 mM phosphate buffer, 150 mM NaCl, pH 7.5) three times for 3 minutes on the shaking table. HRP labeled anti-mouse immunoglobulin was added thereto at a dilution of 1:1000, and the reaction mixture was incubated for an hour. This was washed with PBS (10 mM phosphate buffer, 150 mM NaCl, pH 7.5) three times for 3 minutes. Then, the resultant was immersed in a solution containing a coloring substrate TMBZ to effect coloring. Colored spots were visually identified, to determine polypeptide sequences recognized by the antibodies. Meanwhile, the above 73 polypeptides are referred to as polypeptide Nos. 1 to 73 in order from the N terminal.

For the monoclonal antibody TB001, coloring at polypeptide Nos. 22 to 25 was identified. From the colored spots, it was confirmed that it recognized a sequence of IAQTRDKFL (SEQ ID NO: 2) which corresponds to the amino acid sequence of SEQ ID NO: 1 between residues 70 and 78 from the N-terminal.

For the monoclonal antibody TB002, coloring at polypeptide Nos. 32 to 35 was identified. From the colored spots, it was confirmed that it recognized a sequence of AIPPRGROAVVL (SEQ ID NO: 3) which corresponds to the amino acid sequence of SEQ ID NO: 1 between residues 103 and 114 from the N-terminal.

For the monoclonal antibody TB003, coloring at polypeptide Nos. 59 to 64 was identified. From the colored spots, it was confirmed that it recognized a sequence of PVNYQNFAV (SEQ ID NO: 4) which corresponds to the amino acid sequence of SEQ ID NO: 1 between residues 184 and 192 from the N-terminal.

Example 3

Preparation of an Immunochromatographic Kit Using anti-MPB64 Type Antibody (1) Preparation of Anti-MPB64 Antibody Each clone obtained in Example 1 was inoculated into the abdominal cavity of a mouse, to obtain ascites containing an anti-MPB64 antibody. Further, IgG purification was carried out according to an ordinary method using a protein G adsorbent, to obtain an anti-MPB64 antibody.

(2) Preparation of Gold Colloidal Particle Solution 1 ml of a 1% (v/w) aqueous chloroauric acid solution was added to 99 ml of extra pure water boiled by heating. One minute later, 1.5 ml of a 1% (v/w) aqueous sodium citrate solution was further added thereto, and the mixture was then heated and boiled for 5 minutes. Thereafter, the solution was left at room temperature, so that it was cooled. Subsequently, a 200 mM aqueous potassium carbonate solution was added to the solution, so that the solution was adjusted to pH 9.0. Thereafter, extra pure water was added thereto to adjust the total amount to 100 ml, thereby obtaining a gold colloidal particle solution.

(3) Preparation of Gold Colloidal Particle-Labeled Anti-MPB64 Antibody Solution

The anti-MPB64 antibody obtained above in (1) was labeled with gold colloidal particles by the following procedures.

1 μg equivalent to weight of protein of an anti-MPB64 antibody (hereinafter, when weight of protein of an antibody is shown, it is simply shown as a weight value obtained by gravimetric analysis of a purified protein thereof) was mixed with 1 ml of the gold colloidal particle solution described above in (2), and the mixture was then left at rest at room temperature for 2 minutes, so that all the antibodies were allowed to bind to the surfaces of the gold colloidal particles. Thereafter, a 10% aqueous bovine serum albumin (hereinafter referred to as "BSA") solution was added to the gold colloidal particle solution to adjust the final concentration to 1%, and the residual surfaces of the gold colloidal particles were all blocked with the BSA, to obtain a gold colloidal particle-labeled anti-MPB64 antibody (hereinafter referred to as "the gold colloidal particle-labeled antibody") solution. This solution was centrifuged (5600×G, 30 minutes) to precipitate the gold colloidal particle-labeled antibody. A supernatant solution was eliminated, to obtain the gold colloidal particle-labeled antibody. This gold colloidal particle-labeled antibody was suspended in a 50 mM Tris-HCl buffer (pH 7.4) containing 10% saccharose, 1% BSA and 0.5% Triton-X100, to obtain a gold colloidal particle-labeled antibody solution.

(4) Preparation of Immunochromatographic Test Strip for MPB64 Assay

The immunochromatographic test strip shown in FIG. 1 was produced by the following procedures.

(4-1) Capturing zone for the complex of the MPB64 and the gold colloidal particle-labeled antibody An elongated strip-shaped nitrocellulose membrane with a size of 5 mm width and 36 mm length was prepared as a membrane carrier 3 for chromatographic development of a chromatographic media.

0.5 μL of a solution containing 1.0 mg/ml anti-MPB64 antibody was applied in a linear form to a position 7.5 mm from the end on the starting point side of the chromatographic development of the membrane carrier 3 for chromatographic development. It was dried at room temperature, to form a capturing zone 31 for capturing a complex of the MPB64 protein and the gold colloidal particle-labeled antibody. The monoclonal antibody TB003 was used as the anti-MPB64 antibody.

(4-2) Preparation of the Impregnated Member Impregnated with the Gold Colloidal Particle-Labeled Antibody A strip-shaped glass fiber nonwoven fabric with a size of 5 mm×15 mm was impregnated with 37.5 μL of the gold colloidal particle-labeled antibody solution, and then dried at room temperature, to obtain a gold colloidal particle-labeled antibody impregnated member 2. The monoclonal antibodies TB001 and TB002 labeled with gold colloidal particles were used as the gold colloidal particle-labeled antibody.

(4-3) Preparation of Immunochromatographic Test Strip

In addition to the above membrane carrier 3 for chromatographic development and the above impregnated member 2 containing the labeled-antibody, a cotton fabric as the sample-receiving member 5 and a filter paper as the absorbing member 4 were prepared. Then, a chromatographic test strip which was the same as FIG. 1 was prepared using these members.

Example 4

Sensitivity Comparison with CAPILIA TB (Trade Name; Manufactured By TAUNS LABORATORIES INC.)

The immunochromatographic test strip prepared in Example 3 (in which the monoclonal antibody TB003 was used as an anti-MPB64 antibody which was immobilized in the capturing zone, and the monoclonal antibody TB001 was used as an anti-MPB64 antibody of the gold colloidal particle-labeled antibody) was provided.

*Mycobacterium bovis* BCG Tokyo strain was cultured in Middlebrook 7H11 broth, and the resulting culture supernatant (corresponding to McFarland No. 1, $1 \times 10^8$ cfu/ml in concentration) was diluted with a sample diluent to obtain a test sample. Then, using a micropipette, 100 μL of the test sample was added dropwise to the sample-receiving member 5 of the above test strip, so that it was developed chromatographically therein. It was left at room temperature for 15 minutes. Thereafter, the amount of the complex of the MPB64 protein and the gold colloidal particle-labeled antibody captured by the above capturing zone 31 was observed by naked eyes. The amount of the complex captured was determined by classifying the level of red-violet color, which increases or decreases depending on the captured amount, into the following 4 stages with naked eyes: − (no coloration); ± (slight coloration); + (clear coloration); and ++ (clearer coloration). The Middlebrook 7H11 broth was used as a negative control. As a control immunochromatographic test strip, a commercially available immunochromatographic test kit "CAPILIA TB (trade name; TAUNS LABORATORIES INC.)" was used, and the same test was carried out. The results are shown in Table 1.

TABLE 1

| Sample dilution magnification | CAPILIA TB | The present method |
|---|---|---|
| Blank | − | − |
| ×12800 | − | + |
| ×6400 | ± | + |
| ×3200 | + | + |
| ×1600 | + | ++ |
| ×800 | ++ | ++ |

As clear from Table 1, it was found that the test strip produced in Example 3 had about four times higher sensitivity than the control CAPILIA TB.

Example 5

Cross Reactivity Test

Using the immunochromatographic test strip prepared in Example 3 (the monoclonal antibody TB003 was used as an anti-MPB64 antibody immobilized in the capturing zone, and the monoclonal antibody TB002 was used as an anti-MPB64 antibody of the gold colloidal particle-labeled antibody), reactivity test on *Mycobacterium tuberculosis* complex and various non-tuberculous *Mycobacteria* was conducted. The cultured strains were each diluted with a sample diluent to prepare a test sample. Then, 100 μL of the test sample was added dropwise, so that it was developed chromatographically. After it was left at room temperature for 15 minutes, visual determination was carried out. Using a commercially available immunochromatographic test kit "CAPILIA TB (trade name; manufactured by TAUNS LABORATORIES INC.)" as a control, the same test was carried out. The results are shown in Table 2.

TABLE 2

| Species | Test strip of Example 3 | CAPILIA TB |
|---|---|---|
| *M. tuberculosis* | + | + |
| *M. bovis* | + | + |
| *M. bovis* BCG-Tokyo | + | + |
| *M. marinum* (ATCC 11565) | − | + |
| *M. marinum* (ATCC 11564) | − | + |
| *M. marinum* (ATCC 927) | − | + |
| *M. marinum* (ATCC BAA-535) | − | − |

As clear from Table 2, the test strip of Example 3 showed a reactivity only to *Mycobacterium tuberculosis* complex, i.e., *M. tuberculosis, M. bovis* and *M. bovis* BCG-Tokyo strains, but did not show any cross reactivity to *M. marinum* JATA22-01, 351-2 and 329 which was confirmed on the control CAPILIA TB. Thus, it was shown that the test strip had the specificity to *Mycobacterium tuberculosis* complex which produced MPB64.

Also, the same results were shown for the immunochromatographic test strip in which the monoclonal antibody TB003 was used as an anti-MPB64 antibody immobilized in the capturing zone, and the monoclonal antibody TB001 was used as an anti-MPB64 antibody of the gold colloidal particle-labeled antibody).

Example 6

Preparation of a Fluorescent Immunochromatographic Test Strip Using an Anti-MPB64 Antibody (1) Preparation of Anti-MPB64 Antibody Each clone obtained in Example 1 was inoculated into the abdominal cavity of a mouse, to obtain ascites containing an anti-MPB 64 antibody. Further, IgG purification was carried out according to an ordinary method using a protein G adsorbent, to obtain an anti-MPB 64 antibody.

(2) Preparation of a Fluorescent Latex Particle-Labeled Anti-MPB64 Antibody Solution The anti-MPB64 antibodies obtained above in (1) were respectively labeled with fluorescent latex particles by the following procedures.

1 μg equivalent to weight of protein of the anti-MPB64 antibody (hereinafter, when weight of protein of an antibody is shown, it is simply shown as a weight value obtained by gravimetric analysis of a purified protein thereof) was mixed with 1 ml of a 0.0002% (g/v) fluorescent latex particle suspension, and the mixture was then left at rest at room temperature for 2 minutes, so that all the antibodies were allowed to bind to the surfaces of the fluorescent latex particles. Thereafter, a 10% aqueous bovine serum albumin (hereinafter, referred to as "BSA") solution was added to the fluorescent latex particle suspension to adjust the final concentration to 1%, and the residual surfaces of the fluorescent latex particles were all blocked with the BSA, to obtain a fluorescent latex particle-labeled anti-MPB64 antibody (hereinafter, referred to as "fluorescent latex particle-labeled antibody") solution. This solution was centrifuged (5600×G, 30 minutes) to precipitate the fluorescent latex particle-labeled antibody. A supernatant solution was eliminated, to obtain the fluorescent latex particle-labeled antibody. This fluorescent latex particle-labeled antibody was suspended in a 50 mM Tris-HCl buffer (pH 7.4) containing 10% saccharose, 1% BSA and 0.5% Triton-X100, to obtain a fluorescent latex particle-labeled antibody solution.

(3) Preparation of Immunochromatographic Test Strip for MPB64 Assay

The immunochromatographic test strip shown in FIG. 1 was produced by the following procedures.

(3-1) Capturing Zone for the Complex of the Anti-MPB64 Antibody and the Fluorescent Latex Particle-Labeled Antibody An elongated strip-shaped nitrocellulose membrane with a size of 5 mm width and 36 mm length was prepared as a membrane carrier 3 for chromatographic development of a chromatographic media.

0.5 μL of a solution containing 1.0 mg/ml anti-MPB64 antibody was applied in a linear form to a position 7.5 mm from the end on the starting point side of the chromatographic development in the membrane carrier 3 for chromatographic development. It was dried at room temperature, to form a capturing zone 31 for capturing a complex of the MPB64 protein and the fluorescent latex particle-labeled antibody. The monoclonal antibody TB003 was used as the anti-MPB64 antibody.

(3-2) Preparation of the Impregnated Member Impregnated with the Fluorescent Latex Particle-Labeled Antibody A strip-shaped glass fiber nonwoven fabric with a size of 5 mm×15 mm was impregnated with 37.5 μL of the fluorescent latex particle-labeled antibody solution, and then dried at room temperature, to obtain a fluorescent latex particle-labeled antibody impregnated member 2. The monoclonal antibody TB001 was used as the fluorescent latex particle-labeled antibody.

(3-3) Preparation of Immunochromatographic Test Strip

In addition to the above membrane carrier 3 for chromatographic development and the above impregnated member 2 containing the labeled-antibody, a cotton fabric as the sample-receiving member 5 and a filter paper as the absorbing member 4 were prepared. Then, a chromatographic test strip which was the same as FIG. 1 was prepared using these members.

Example 7

Sensitivity Comparison with CAPILIA TB (Trade Name; Manufactured by TAUNS LABORATORIES INC.)

The fluorescent immunochromatographic test strip prepared in Example 6 (in which the monoclonal TB003 was used as an anti-MPB64 antibody which was immobilized in a capturing zone, and the monoclonal antibody TB001 was used as an anti-MPB64 of the fluorescent latex particle-labeled antibody) was provided.

*Mycobacterium bovis* BCG Tokyo strain was cultured in Middlebrook 7H11 broth, and the resulting culture supernatant (corresponding to McFarland No. 1, 1×10$^8$ cfu/ml in concentration) was diluted with a sample diluent to obtain a test sample. Then, using a micropipette, 100 μl, of the test sample was added dropwise to the sample-receiving member 5 of the above test strip, so that it was developed chromatographically therein. It was left at room temperature for 15 minutes. Thereafter, the amount of the complex of the MPB64 protein and the fluorescent latex particle-labeled antibody captured by the above capturing zone 31 was measured by the fluorescent immunochromatographic reader (manufactured by Hamamatsu Photonics K.K.). The Middlebrook 7H11 broth was used as a negative control. As a control immunochromatographic test strip, a commercially available immunochromatographic test kit "CAPILIA TB (trade name; TAUNS LABORATORIES INC.)" was used, and the same test was carried out, and the amount of the complex with the gold colloidal particle-labeled antibody captured was measured by the immunochromatographic reader (manufactured by Hamamatsu Photonics K.K.). Detection sensitivity was compared about the dilution magnification of the sample at which the minimum detection sensitivity was shown. The results are shown in Table 3.

TABLE 3

| Sample dilution magnification | CAPILIA ® TB Absorbance | Test strip of Example 6 Fluorescence intensity |
| --- | --- | --- |
| Blank | 0 | 0.0 |
| ×204800 | 0.1 | 5.6 |
| ×102400 | 0.3 | 11.1 |
| ×51200 | 0.6 | 22.2 |
| ×25600 | 1.2 | 44.3 |
| ×12800 | 1.5 | 88.6 |
| ×6400 | 5.4 | 177.1 |

From Table 3, the detection limit of CAPILIA TB was 6400-fold diluted sample whilst the detection limit of the fluorescent immunochromatographic test strip prepared in Example 6 was 204800-fold. Therefore, it was found that the fluorescent immunochromatographic test strip prepared in Example 6 had about 32-fold higher sensitivity than the control CAPILIA TB.

Example 8

MPT64 Assay in Sputum Derived from Tubercular Patient

Sputa were collected from patients who were clinically diagnosed as having tuberculosis to obtain samples. The collected sputum samples were subjected to treatment with protease and treatment with N-acetyl-L-cysteine/sodium hydroxide (hereinafter, referred to as NALC-NaOH method) for making them uniform. The pretreated samples were each applied to a slide glass to obtain a smear preparation. The smear preparation was Ziehl-Neelsen stained and observed with a microscope. Determination was made based on Guideline for Mycobacterial Examination 2007. For the number of bacteria detected, 1-9 AFB/100 microscopic fields is represented by +, ≥10 AFB/100 microscopic fields is represented by 2+, and ≥10 AFB/1 microscopic fields is represented by 3+. To 1 mL of the sputum sample determined by the smear examination, a semi-alkali protease solution (trade name; SPUTAZYME, manufactured by KYOKUTO PHARMACEUTICAL INDUSTRIAL CO., LTD.) was added, and treated at room temperature. After centrifuging, the NALC-NaOH solution was added to the residue, the mixture was mixed for a few seconds by a vortex mixer, and phosphate buffer (pH 7.0) was added thereto for neutralization. After centrifuging, the residue was resuspended in a PBS containing 0.1% Tween 80, and physically treated by adding glass beads and stirring, to obtain a test sample. Using a micropipette, 100 µL of the test sample was added dropwise to the sample-receiving number 5 of the test strip obtained in Example 6, so that it was developed chromatographically therein. It was left at room temperature for 15 minutes. Thereafter, the amount of the complex of the MPB64 protein and the fluorescent latex particle-labeled antibody captured by the above capturing zone 31 was measured by a fluorescent immunochromatographic reader (manufactured by Hamamatsu Photonics K.K.). A sputum collected from a normal person with tuberculosis infection was treated in the same manner as above, and used as a negative control. As a control test strip, a commercially available immunochromatographic test strip "CAPILIA TB (trade name; TAUNS LABORATORIES INC.)" was used, and the same test was carried out. The results are shown in Table 4 and FIG. 2.

TABLE 4

| Sample number | Smear examination | CAPILIA TB Absorbance | Test strip of Example 6 Fluorescence intensity |
| --- | --- | --- | --- |
| 1 | + | 0 | 0 |
| 2 | + | 0 | 0 |
| 3 | + | 0 | 3.6 |
| 4 | 2+ | 0 | 27.2 |
| 5 | 2+ | 0 | 69.3 |
| 6 | 3+ | 0 | 201.2 |
| 7 | 3+ | 0 | 493.5 |
| 8 | 3+ | 23 | 1071.7 |

Figure 2:
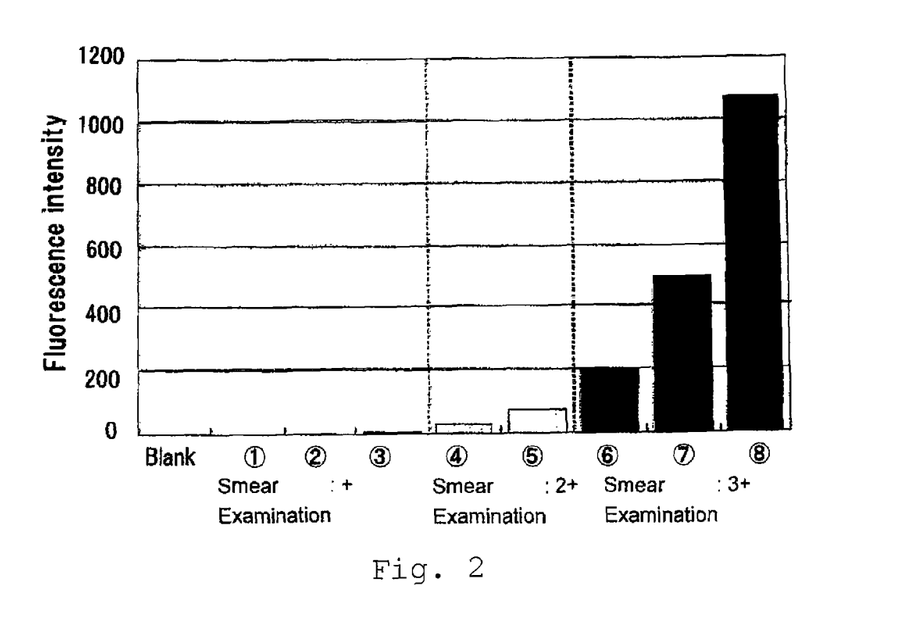
FIG. 2 is a graph showing the results of Example 8.

As it is clear from Table 4 and FIG. 2, it was found that the fluorescent immunochromatographic test strip prepared in Example 6 had higher sensitivity than the control CAPILIA TB.

Example 9

Preparation of Platinum-Gold Colloidal Particle-Labeled Immunochromatographic Test Strip Using the Anti-MPB64 Antibody (1) Preparation of Anti-MPB64 Antibody Each clone obtained in Example 1 was inoculated into the abdominal cavity of a mouse, to obtain ascites containing an anti-MPB64 antibody. Further, IgG purification was carried out according to an ordinary method using a protein G adsorbent, to obtain an anti-MPB64 antibody.

(2) Preparation of Platinum-Gold Colloidal Particle

All the laboratory glass wears to be used were washed with aqua regia. 390 ml of extra pure water was placed in a flask and boiled, and 30 ml of chloroauric acid solution (corresponding to 1 g of gold per 1 L of the solution, manufactured by KATAYAMA CHEMICAL INC.) was added to the boiled water. Then, 60 ml of 1 wt. % sodium citrate solution was added thereto, and after 6 minutes and 45 seconds, 30 ml of chloroplatinic acid solution (corresponding to 1 g of platinum per 1 L of the solution, manufactured by Wako Pure Chemical Industries, Ltd.) was added thereto. 5 minutes after the addition of chloroplatinic acid solution, 60 ml of a 1 wt. % aqueous sodium citrate solution was added thereto, and reduced for 4 hours to obtain a platinum-gold colloidal particle suspension.

(3) Preparation of Platinum-Gold Colloidal Particle-Labeled Anti-MPB64 Antibody Solution The anti-MPB64 antibody obtained above in (1) was labeled with platinum-gold colloidal particles by the following procedures.

1 µg equivalent to weight of protein of an anti-MPB64 antibody (hereinafter, when weight of protein of an antibody is shown, it is simply shown as a weight value obtained by gravimetric analysis of a purified protein thereof) was mixed with 1 ml of a platinum-gold colloidal particle solution described above in (2), and the mixture was then left at rest at room temperature for 2 minutes, so that all the antibodies were allowed to bind to the surfaces of the platinum-gold colloidal particles. Thereafter, a 10% aqueous bovine serum albumin (hereinafter referred to as "BSA") solution was added to the platinum-gold colloidal particle solution to adjust the final concentration to 1%, and the residual surfaces of the platinum-gold colloidal particles were all blocked with the BSA, to obtain a platinum-gold colloidal particle-labeled anti-MPB64 antibody (hereinafter referred to as "the platinum-gold colloidal particle-labeled antibody") solution. This solution was centrifuged (5600×G, 30 minutes) to precipitate the platinum-gold colloidal particle-labeled antibody. A supernatant solution was eliminated, to obtain the platinum-gold colloidal particle-labeled antibody. This platinum-gold colloidal particle-labeled antibody was suspended in a 50 mM Tris-HCl buffer (pH 7.4) containing 10% saccharose, 1% BSA and 0.5% Triton-X100, to obtain a platinum-gold colloidal particle-labeled antibody solution.

(4) Preparation of Immunochromatographic Test Strip for MPB64 Assay

The immunochromatographic test strip shown in FIG. 1 was produced by the following procedures.

(4-1) Capturing zone for the complex of the MPB64 and platinum-gold colloidal particle-labeled antibody.

An elongated strip-shaped nitrocellulose membrane with a size of 5 mm width and 36 mm length was prepared as a membrane carrier 3 for chromatographic development of a chromatographic media.

0.5 µL of a solution containing 1.0 mg/ml anti-MPB64 antibody was applied in a linear form to a position 7.5 mm from the end on the starting point side of the chromatographic development in the membrane carrier 3 for chromatographic development. It was dried at room temperature, to form a capturing zone 31 for capturing the complex of the MPB64 protein and the platinum-gold colloidal particle-labeled antibody. The monoclonal antibody TB003 was used as the anti-MPB64 antibody.

(4-2) Preparation of the Impregnated Member Impregnated with the Platinum-Gold Colloidal Particle-Labeled Antibody A strip-shaped glass fiber nonwoven fabric with a size of 5 mm×15 mm was impregnated with 37.5 µL of the platinum-gold colloidal particle-labeled antibody solution, and then dried at room temperature, to obtain a platinum-gold colloidal particle-labeled antibody impregnated member 2. The monoclonal antibodies TB001 and TB002 labeled with gold colloidal particles were used as the platinum-gold colloidal particle-labeled antibody.

(4-3) Preparation of Immunochromatographic Test Strip

In addition to the above membrane carrier 3 for chromatographic development and the above impregnated member 2 containing the labeled-antibody, a cotton fabric as the sample-receiving member 5 and a filter paper as the absorbing member 4 were prepared. Then, a chromatographic test strip which was the same as FIG. 1 was prepared using these members.

Example 10

Sensitivity Comparison with CAPILIA TB (Trade Name; Manufactured by TAUNS LABORATORIES INC.)

(1) Immunochromatographic Test Strip

The platinum-gold colloidal particle-labeled immunochromatographic test strip prepared in Example 9 (in which the monoclonal TB003 was used as an antibody which was immobilized in a capturing zone, and the monoclonal antibody TB001 was used as an anti-MPB64 antibody of the platinum-gold colloidal particle-labeled antibody) was provided.

(2) Preparation of Liquid Medium 4.7 g of Middlebrook 7H11 broth Base (manufactured by Difco) was dissolved in 900 ml of a distilled water containing 0.5 g of Tween 80. It was sterilized under high pressure at 121° C. for 10 minutes in an autoclave. After cooling, 100 ml of ADC Enrichment (albumin-dextrose-catalase) was aseptically added thereto, and 200 μL each was aliquoted in a 1.5 mL microtube. MGIT (manufactured by Nippon Becton Dickinson Company, Ltd.) was used as a control culturing medium.

(3) Culturing of Biological Sample

Using a Middlebrook 7H11 broth prepared by the same method as above, *Mycobacterium bovis* BCG Tokyo strain was cultured to obtain bacterial cells. The bacterial cells were adjusted to be equivalent to Mcfarland No. 1 ($1 \times 10^8$ cfu/ml in concentration), to obtain a standard bacterial culture. This standard bacterial culture was added to a sputum collected from a normal person to adjust the final concentration to $10^4$ cfu/ml, so that a false positive sputum sample was prepared. This false positive sputum sample was treated with the NALC-NaOH method and centrifuged to obtain pellets. Phosphate buffered physiological saline (hereinafter referred to as PBS) containing Tween 80 was added to the pellets, followed by washing. The supernatant was eliminated by centrifuging, and the remaining was resuspended in PBS containing Tween 80, and 100 μL thereof was inoculated to each culturing medium.

After culturing for a few days, a supernatant was collected from each of the culture media to obtain a test sample. Then, using a micropipette, 100 μL of the test sample was added dropwise to the sample-receiving member 5 of the above test strip, so that it was developed chromatographically therein. It was left at room temperature for 15 minutes. Thereafter, the amount of the complex of the MPB64 protein and the metallic colloidal particle-labeled antibody captured by the above capturing zone 31 was observed by naked eyes. The captured amount was determined by visually observing degree of coloring which increases or decreases in proportion to the captured amount, and classifying it into the following 4 stages: − (no coloration); ± (slight coloration); + (clear coloration); and ++ (significantly clear coloration). The results are shown in Table 5.

TABLE 5

| Incubation days | Test strip of Example 9 | CAPILIA ® TB |
|---|---|---|
| Day 0 | − | − |
| Day 1 | − | − |
| Day 2 | ± | − |
| Day 5 | ++ | + |

Even on day 5, no fluorescence was detected in MGIT which was a control culturing medium. Fluorescence was detected therein due to the growth of bacteria on day 10.

From the above results, it is possible to detect the bacteria in a shorter period of time than the conventional method by testing in accordance with the present detection method after culturing for a short time before the bacteria substantially start to grow.

INDUSTRIAL APPLICABILITY

The present invention provides an immunoassay using an antibody to a *Mycobacterium tuberculosis* complex-specific secretory protein MPB64, and more specifically relates to a sandwich immunoassay, and particularly an immunochromatographic assay and an immunochromatographic test strip. The present invention enables *Mycobacterium tuberculosis* complex to be detected specifically with high sensitivity, and thus is useful for a rapid, safe and highly accurate diagnosis of infection with *Mycobacterium tuberculosis* complex.

BRIEF DESCRIPTION OF DRAWINGS

FIG. 1a is a plain view of an immunochromatographic test strip, and FIG. 1b is a longitudinal view in section of the immunochromatographic test strip shown in FIG. 1a.

DESCRIPTION OF SYMBOLS

1 Adhesive sheet
2 Impregnated member
3 Membrane carrier
31 Capturing zone
4 Absorbing member
5 Sample-receiving member

The invention claimed is:

1. A method for detecting *Mycobacterium tuberculosis* complex, which comprises an immunoassay using an antibody to a *Mycobacterium tuberculosis* complex-specific secretory protein MPB64, in which said antibody comprises a monoclonal antibody to an epitope of MPB64 located in any one of amino acid sequences of SEQ ID NOS: 2, 3 or 4.

2. A method for detecting *Mycobacterium tuberculosis* complex, which comprises a sandwich immunoassay using first and second antibodies to a *Mycobacterium tuberculosis* complex-specific secretory protein MPB64, in which at least one of the first and second antibodies comprises a monoclonal antibody to an epitope of MPB64 located in any one of amino acid sequences of SEQ ID NOS: 2, 3 or 4.

3. The detection method according to claim 2, wherein either of the first and second antibodies is immobilized to a carrier.

4. The detection method according to claim 2, wherein a biological sample is subjected to said immunoassay without culturing or after culturing for a time sufficient for secreting a detectable amount of MPB64 before the *Mycobacterium tuberculosis* complex bacteria in the sample start to grow.

5. The detection method according to claim 4, wherein said biological sample is subjected to a treatment for inactivation of *Mycobacterium tuberculosis* or a pretreatment by dispersion or solubilization before subjected to the immunoassay.

6. The detection method according to claim 5, wherein said treatment by dispersion or solubilization is carried out by stirring operation, or by addition to the biological sample of at least one member selected from the group consisting of an alkali substance, a reducing substance, a protease and a surfactant.

7. The detection method according to any one of claims 4 to 6, wherein said biological sample is sputum.

8. An immunochromatographic assay for detecting *Mycobacterium tuberculosis* complex, which comprises:
   providing a membrane carrier having a capturing zone which is formed in a predetermined position thereof by immobilizing a first antibody to a *Mycobacterium tuberculosis* complex-specific secretory protein MPB64,
   chromatographically developing a mixed solution in the membrane carrier toward the capturing zone, the mixed solution containing a second antibody to the MPB64 and a predetermined amount of a test sample,
   whereby a complex of an antigen contained in the test sample and the second antibody is captured by the capturing zone,
wherein at least one of the first and second antibodies comprises a monoclonal antibody to an epitope of MPB64 located in any one of amino acid sequences of SEQ ID NOS: 2, 3 or 4.

9. The immunochromatographic assay according to claim 8, wherein said test sample contains a biological sample which has not been cultured or has been cultured for a time sufficient for secreting a detectable amount of MPB64 before the *Mycobacterium tuberculosis* complex bacteria in the sample start to grow.

10. The immunochromatographic assay according to claim 9, wherein said biological sample is pretreated by treatment for inactivation of *Mycobacterium tuberculosis*, or treatment by dispersion or solubilization.

11. The immunochromatographic assay according to claim 10, wherein said treatment by dispersion or solubilization of the biological sample is carried out by stirring operation, or by addition to the biological sample of at least one member selected from the group consisting of an alkali substance, a reducing substance, a protease and a surfactant.

12. The immunochromatographic assay according to any one of claims 9 to 11, wherein said biological sample is sputum.

13. The immunochromatographic assay according to claim 8, wherein the second antibody is labeled with a metallic colloidal particle or a latex particle.

14. The immunochromatographic assay according to claim 13, wherein the membrane carrier is a nitro cellulose membrane.

15. An immunochromatographic test strip for detecting a *Mycobacterium tuberculosis* complex, which at least comprises first and second antibodies to a *Mycobacterium tuberculosis* complex-specific secretory protein MPB64, and a membrane carrier, wherein the first antibody is previously immobilized in a predetermined position of the membrane carrier so as to form a capturing zone, the second antibody is labeled with a suitable labeling agent and is prepared at a position remote from the capturing zone for being chromatographically developed in the membrane carrier, wherein at least one of the first and second antibodies comprises a monoclonal antibody to an epitope of MPB64 located in any one of amino acid sequences of SEQ ID NOS: 2, 3 or 4.

16. The immunochromatographic test strip according to claim 15, wherein the second antibody is labeled with a metallic colloidal particle or a latex particle.

17. The immunochromatographic test strip according to claim 16, wherein the membrane carrier is a nitro cellulose membrane.

18. A monoclonal antibody selected from the group consisting of:
   (a) a monoclonal antibody which recognizes an epitope of MPB64 located in SEQ ID NO:2;
   (b) a monoclonal antibody which recognizes an epitope of MPB64 located in SEQ ID NO:3; and
   (c) a monoclonal antibody which recognizes an epitope of MPB64 located in SEQ ID NO:4.

19. A monoclonal antibody according to claim 18, wherein said monoclonal antibody recognizes an epitope of MPB64 located in SEQ ID NO:2.

20. A monoclonal antibody according to claim 18, wherein said monoclonal antibody recognizes an epitope of MPB64 located in SEQ ID NO:3.

21. A monoclonal antibody according to claim 18, wherein said monoclonal antibody recognizes an epitope of MPB64 located in SEQ ID NO:4.

22. The detection method according to claim 1, wherein said antibody comprises a monoclonal antibody to an epitope of MPB64 located in the amino acid sequence of SEQ ID NO:2.

23. The detection method according to claim 1, wherein said antibody comprises a monoclonal antibody to an epitope of MPB64 located in the amino acid sequence of SEQ ID NO:3.

24. The detection method according to claim 1, wherein said antibody comprises a monoclonal antibody to an epitope of MPB64 located in the amino acid sequence of SEQ ID NO:4.

25. The detection method according to claim 2, wherein said antibody comprises a monoclonal antibody to an epitope of MPB64 located in the amino acid sequence of SEQ ID NO:2.

26. The detection method according to claim 2, wherein said antibody comprises a monoclonal antibody to an epitope of MPB64 located in the amino acid sequence of SEQ ID NO:3.

27. The detection method according to claim 2, wherein said antibody comprises a monoclonal antibody to an epitope of MPB64 located in the amino acid sequence of SEQ ID NO:4.

28. The immunochromatographic assay according to claim 8, wherein at least one of the first and second antibodies comprises a monoclonal antibody to an epitope of MPB64 located in amino acid sequence of SEQ ID NO: 2.

29. The immunochromatographic assay according to claim 8, wherein at least one of the first and second antibodies comprises a monoclonal antibody to an epitope of MPB64 located in the amino acid sequence of SEQ ID NO:3.

30. The immunochromatographic assay according to claim 8, wherein at least one of the first and second antibodies comprises a monoclonal antibody to an epitope of MPB64 located in the amino acid sequence of SEQ ID NO:4.

31. The immunochromatographic test strip according to claim 15, wherein at least one of the first and second antibodies comprises a monoclonal antibody to an epitope of MPB64 located in amino acid sequence of SEQ ID NO: 2.

32. The immunochromatographic test strip according to claim 15, wherein at least one of the first and second antibodies comprises a monoclonal antibody to an epitope of MPB64 located in amino acid sequence of SEQ ID NO: 3.

33. The immunochromatographic test strip according to claim 15, wherein at least one of the first and second antibodies comprises to a monoclonal antibody epitope of MPB64 located in amino acid sequence of SEQ ID NO: 4.

34. The detection method according to claim 6, wherein said treatment by dispersion or solubilization of the biological sample is carried out by addition to the biological sample of at least one member selected from the group consisting of an alkali substance, a reducing substance and a protease.

35. The immunochromatographic assay according to claim 11, wherein said treatment by dispersion or solubilization of the biological sample is carried out by addition to the biological sample of at least one member selected from the group consisting of an alkali substance, a reducing substance and a protease.

36. The detection method according to claim 6, wherein said treatment by dispersion or solubilization of the biological sample is carried out by addition to the biological sample of an alkali substance and a reducing substance.

37. The detection method according to claim 11, wherein said treatment by dispersion or solubilization of the biological sample is carried out by addition to the biological sample of an alkali substance and a reducing substance.

* * * * *

SEQUENCE LISTING

<160> NUMBER OF SEQ ID NOS: 4

<210> SEQ ID NO 1
<211> LENGTH: 228
<212> TYPE: PRT
<213> ORGANISM: Mycobacterium tuberculosis -continued

<400> SEQUENCE: 1

```
Met Arg Ile Lys Ile Phe Met Leu Val Thr Ala Val Leu Leu Cys
1               5                   10                  15

Cys Ser Gly Val Ala Thr Ala Ala Pro Lys Thr Tyr Cys Glu Glu Leu
            20                  25                  30

Lys Gly Thr Asp Thr Gly Gln Ala Cys Gln Ile Gln Met Ser Asp Pro
        35                  40                  45

Ala Tyr Asn Ile Asn Ile Ser Leu Pro Ser Tyr Tyr Pro Asp Gln Lys
    50                  55                  60

Ser Leu Glu Asn Tyr Ile Ala Gln Thr Arg Asp Lys Phe Leu Ser Ala
65                  70                  75                  80

Ala Thr Ser Ser Thr Pro Arg Glu Ala Pro Tyr Glu Leu Asn Ile Thr
                85                  90                  95

Ser Ala Thr Tyr Gln Ser Ala Ile Pro Pro Arg Gly Thr Gln Ala Val
            100                 105                 110

Val Leu Lys Val Tyr Gln Asn Ala Gly Gly Thr His Pro Thr Thr Thr
        115                 120                 125

Tyr Lys Ala Phe Asp Trp Asp Gln Ala Tyr Arg Lys Pro Ile Thr Tyr
    130                 135                 140

Asp Thr Leu Trp Gln Ala Asp Thr Asp Pro Leu Pro Val Val Phe Pro
145                 150                 155                 160

Ile Val Gln Gly Glu Leu Ser Lys Gln Thr Gly Gln Val Ser Ile
                165                 170                 175

Ala Pro Asn Ala Gly Leu Asp Pro Val Asn Tyr Gln Asn Phe Ala Val
            180                 185                 190

Thr Asn Asp Gly Val Ile Phe Phe Asn Pro Gly Glu Leu Leu Pro
                195                 200                 205

Glu Ala Ala Gly Pro Thr Gln Val Leu Val Pro Arg Ser Ala Ile Asp
    210                 215                 220

Ser Met Leu Ala
225
```

<210> SEQ ID NO 2
<211> LENGTH: 9
<212> TYPE: PRT
<213> ORGANISM: Mycobacterium tuberculosis

<400> SEQUENCE: 2

```
Ile Ala Gln Thr Arg Asp Lys Phe Leu
1               5
```

<210> SEQ ID NO 3
<211> LENGTH: 12
<212> TYPE: PRT
<213> ORGANISM: Mycobacterium tuberculosis

<400> SEQUENCE: 3

```
Ala Ile Pro Pro Arg Gly Thr Gln Ala Val Val Leu
1               5                   10
```

<210> SEQ ID NO 4
<211> LENGTH: 9
<212> TYPE: PRT

```
<213> ORGANISM: Mycobacterium tuberculosis

<400> SEQUENCE: 4

Pro Val Asn Tyr Gln Asn Phe Ala Val
1               5
```